| United States Patent [19] | [11] Patent Number: 5,001,059 |
| --- | --- |
| Skatrud et al. | [45] Date of Patent: Mar. 19, 1991 |

[54] L-ASCORBIC ACID PRODUCTION IN MICROORGANISMS

[75] Inventors: Thomas J. Skatrud; Ronald J. Huss, both of Manitowoc, Wis.

[73] Assignee: Bio-Technical Resources, Inc., Manitowoc, Wis.

[21] Appl. No.: 750,828

[22] Filed: Jul. 1, 1985

[51] Int. Cl.$^5$ .......................... C12P 7/58; C12P 7/60; C12N 1/12; C12N 15/00

[52] U.S. Cl. ...................... 435/137; 435/138; 435/257; 435/946; 435/172.1

[58] Field of Search ............... 435/137, 138, 257, 946, 435/172.1; 549/315

[56] References Cited

PUBLICATIONS

McNamer et al., "Proline Up Take and Ultilization by *Chlorella pyrenoidosa*", *Plant Physiol.*, vol. 52, pp. 561–564, 1973.

Gruen et al., "Determination of Ascorbic Acid in Algae by HPLC on Strong Cation-Exchange Resin with Electrochemical Detection", *Anal. Biochem.* 130, pp. 191–198, 1983.

*Primary Examiner*—Elizabeth C. Weimar
*Assistant Examiner*—Irene Marx
*Attorney, Agent, or Firm*—Bertram I. Rowland; Richard L. Neeley

[57] ABSTRACT

Improved production of ascorbic acid is obtained empolying Chlorella as a microorganism source and growing the culture under a controlled pattern of carbon source supply. Greatly improved ratios of ascorbic acid to total carbon supplied as well as enhanced ascorbic acid concentrations in the fermentor are obtained.

*C. pyrenoidosa* UV101-158 was deposited at the A.T.C.C. on June 27, 1985 and given Accession No. 53170.

2 Claims, No Drawings

L-ASCORBIC ACID PRODUCTION IN MICROORGANISMS

BACKGROUND OF THE INVENTION

1. Field of the Invention

L-Ascorbic acid is an important nutrient supplement, which finds wide application, in vitamin capsules and as a nutrient supplement in foods for both humans and other Vitamin C requiring animals. L-Ascorbic acid is basically a bulk chemical which is highly price sensitive and requires economic and efficient production in order to be marketable. Therefore, there is substantial interest in being able to develop processes employing microorganisms which provide for efficient conversion of nutrients resulting in efficient production of L-ascorbic acid.

Wild-type microorganisms produce only minor amounts of L-ascorbic acid. Whether substantially enhanced production of L-ascorbic acid can be achieved with microorganisms is unpredictable. Even where enhanced production of L-ascorbic acid in relation to nutrients consumed might be feasible due to increased expression of enzymes involved in the L-ascorbic acid pathway, the effect of increased concentrations of L-ascorbic acid on the viability and metabolism of the microorganism is unpredictable. Therefore, while it is known that microorganisms produce L-ascorbic acid, there is no certainty that an economically efficient process can be attained.

2. Description of the Prior Art

Loewus, F. A., in L-Ascorbic Acid: Metabolism, Biosynthesis, Function, *The Biochemistry of Plants*, Vol. 3, Academic Press, Inc., pp. 77-99, 1980, provides a review of the sources and biosynthesis of L-ascorbic acid. Descriptions of production of ascorbic acid in algae may be found in Vaidya et al., *Science and Culture* (1971) 37:383-384; Subbulakshmi et al., *Nutrition Reports International* (1976) 14:581-591; Aaronson et al., *Arch. Microbiol.* (1977) 112:57-59; Shigeoka et al., *J. Nutr. Sci. Vitaminol.* (1979) 25:299-307; Shigeoka et al., *Agric. Biol. Chem.* (1979) 43:2053-2058; Bayanova and Trubachev, *Prikladnaya Biokhimiya i Mikrobiologyia* (1981) 17:400-407 (UDC 582.26:577.16); and Ciferri, *Microbiological Reviews* (1983) 47:551-578.

SUMMARY OF THE INVENTION

An improved process for L-ascorbic acid production is provided employing Chlorella algae, whereby the Chlorella is grown to intermediate cell density during an initial phase and growth continued by the sequential or continuous addition of a carbon source at a restricted level. Improved utilization of the carbon source is observed in relation to L-ascorbic acid production, while obtaining an enhanced yield.

DESCRIPTION OF THE SPECIFIC EMBODIMENTS

Novel methods are provided for the efficient production of L-ascorbic acid in microbial cells. The method involves initial growth of algae in a fermentor with a carbon source which is sufficient for the cells to grow to an intermediate density. At the depleted stage, additional amounts of the carbon source are added sequentially or continuously to maintain the carbon source concentration below a predetermined level until the addition is terminated. Termination will normally be governed by the substantial exhaustion of the microorganism to produce L-ascorbic acid.

The microorganism of interest may be randomly screened for strains which are overproducers. Microorganisms showing promise may be selected and mutagenized using physical or chemical mutagenizing agents, e.g. U.V. light, x-rays, nitrosourea, dimethyl sulfate, etc. The detection of overproducers and excretors may be advantageously determined with redox dyes. By employing analogs to metabolic intermediates to ascorbic acid or inhibitors of ascorbic acid synthesis, microorganisms may be selected which are capable of maintaining or increasing L-ascorbic acid production in the presence of the chemical interference.

Progeny of the above procedures are selected for improved specific formation of L-ascorbic acid as measured by milligram/gram of cells. These progeny may then be further separated into individual clones and further subjected to the above procedures. The algae of choice is Chlorella, particularly a strain of *Chlorella pyrenoidosa*. Of particular interest is the *C. pyrenoidosa*, strain UTEX 1663 or other equivalent strain.

In carrying out the process, a nutrient culture medium is inoculated with an actively growing culture of the microorganism strain in amounts sufficient to provide an initial cell density of about 0.15 to 0.4 g/L of dry weight of cells. The culture medium will include the carbon source, a variety of salts and trace metals. The carbon source will normally be a source of glucose, including glucose. The source of glucose may be any saccharide or polysaccharide which can be converted to glucose, e.g., sucrose, amylose, etc. The total amount of glucose source employed would, if not metabolized, provide a concentration of about 65 to 90, more usually about 75 to 85 and preferably about 80 g/L. Usually, about 15% to 30% of the total glucose will be added initially, more usually about 20% to 25% of the total glucose. The glucose will normally be added both initially and during the course of the fermentation with other additives. The glucose source will generally be maintained during the period of unrestricted growth in the range of 15-30 g/L. This amount is found to be sufficient to avoid glucose limitation during the growth period.

Desirably, some of the additives will be present initially in the fermentor and continually augmented by the subsequent additions of the same additives in conjunction with the addition of the glucose source.

Among the additives which will have a different ratio to glucose in the amounts added incrementally as compared to the total amounts added to the fermentor are the alkali metal phosphates, sodium and potassium phosphates, particularly as the dibasic sodium phosphate and the monobasic potassium phosphate. The total amount of the dibasic sodium phosphate will be about 1 to 2 total g/L, usually about 1 to 1.5 total g/L and preferably about 1.3 total g/L. The amount initially present in the fermentor of dibasic sodium phosphate will be about 35% to 50%, more usually about 40% to 45% of the total amount of dibasic sodium phosphate added. The total amount of monobasic potassium phosphate will be about 1.5 to 3 g/L, more usually about 2 to 2.5 g/L. The amount initially present will generally be about 40% to 50% of the total amount, more usually about 45% to 50% of the total amount.

In addition to the above additives, a biologically acceptable chelating agent is added. Conveniently, trisodium citrate will be employed in total amount in from about 0.8 to 1.2 g/L, usually about 1.0 g/L. Monobasic sodium phosphate will be present in from about 0.8 to 1 g/L, preferably about 0.95 to 1 g/L. A biologically acceptable mineral acid is added to maintain the trace metals in solution and also to neutralize the ammonia which is usually employed as the nitrogen source. Conveniently, conc. sulfuric acid is employed in amount of about 1 to 2, more usually about 1.2 to 1.5ml/L. Among the metals, magnesium will be present in about 0.1 to 0.2 g/L, preferably about 0.1 to 0.15 g/L, particularly as a physiologically acceptable salt, e.g., sulfate. The amount of iron and copper which is employed is limited, since these metals repress ascorbic acid formation. Iron (ferrous) will be present initially in from about 5 to 7 mg/L, preferably about 5.5 to 6 mg/L, and will not be included in any subsequent additions. Copper will be present in relatively minute amounts generally from about 1 to 50 μg/g of glucose.

The trace metal solution, which will be described in the Experimental section, will be present in total amount in from about 10 to 15 ml/L, more usually about 12 to 14 ml/L. Based on glucose, the trace metal solution will be employed in from 0.1 to 0.2 ml/g.

Conveniently, a solution is prepared which is added during the course of the fermentation. This solution will have for the most part the following composition.

TABLE 1

Medium Formula

| COMPONENT | CONCENTRATION (relative to glucose) |
|---|---|
| glucose | 1.0 |
| trisodium citrate, dihydrate | 0.0125 |
| magnesium sulfate, anhydrous | 0.0082 |
| monobasic sodium phosphate | 0.0116 |
| monobasic potassium phosphate | 0.0238 |
| dibasic sodium phosphate | 0.0121 |
| trace metal mixture | 0.1675 ml/g |
| sulfuric acid 98% (w/w) | 0.0329 |

Nitrogen supplied is by anhydrous ammonia. This is also used as pH control. Actual N level in media is determined by acidity of media and buffer capacity of media.

The trace metal composition will have the following metals.

TABLE II

Trace Metal Solution

| COMPONENT | CONCENTRATION (conc. in stock solution) mg/liter |
|---|---|
| calcium chloride, dihydrate | 3102 |
| manganese (II) sulfate, monohydrate | 400 |
| copper (II) sulfate, monohydrate | 0.4 |
| cobalt (II) chloride, pentahydrate | 40 |
| boric acid | 160 |
| zinc (II) sulfate, heptahydrate | 400 |
| sodium molybdate, dihydrate | 19 |
| vanadyl sulfate, dihydrate | 20 |
| nickel (II) nitrate, hexahydrate | 8 |
| sodium selenite | 18 |

The stock solution of trace metals is prepared by adding the appropriate amounts of the various compounds indicated in the above table dissolved in distilled water containing a trace of HCl to distilled water, where the final volume is one liter and contains 20 ml of concentrated HCl. Distilled water is used to ensure the proper ratio of component trace metals.

While a number of the salts are referred to as mono- or dibasic salts, it should be understood that this is a matter of convenience and not necessity. These compounds act as buffers and therefore the ratio of the state of protonation will vary with the pH of the medium.

In carrying out a fermentation, dibasic sodium phosphate and monobasic sodium phosphate will be dissolved into about 75% to 90% of the total medium to be added, usually about 80% to 90% of the total medium to be added to the fermentor.

The solution to be added incrementally during the course of the fermentation is then prepared by combining the individual components in proper ratios. The glucose will be dissolved in from about 75% to 85% preferably about 80% of the water to be used. The citrate, magnesium and sulfuric acid are combined in an aqueous medium containing from about 5% to 15%, usually about 10% of the water, while the phosphates are combined in about 5% to 15%, more usually about 10% of the water to be used, followed by the trace metal solution in about 5% to 15%, more usually about 8% to 10% of the total amount of water to be used. To the fermentor containing a portion of the phosphates is added the ferrous salt and about 20% of the above-prepared glucose-salts concentrate. The addition is aseptic, so as to avoid the introduction of any foreign microorganisms. The nutrient medium may then be brought up to the desired temperature, generally in the range of about 30° to 40° C., preferably about 35° C. and the fermentor inoculated with the inoculant to provide from about 0.15 to 0.4 g/L initial cell density. A small amount of antifoaming agent may be added during the progress of the fermentation.

In the first stage of the fermentation, the cells are grown to intermediate density. This will usually involve a period of about 35 to 50 hr, more usually about 40 to 45 hr, with a growth rate of about 0.1 to 0.15 $hr^{-1}$. The pH may be controlled by employing anhydrous ammonia, so as to maintain the pH in the range of about 6.5 to 8.0. Usually the pH control is released after active growth. Agitation will usually be at about 200 to 1000 rpm and aeration about 0.2 to 0.6 L/min of air. The final density for the initial phase should be at about 35 to 45 g/L cell density, preferably about 40 g/L.

The glucose availability is monitored in the supernatant by a convenient means, e.g. glucose oxidase enzyme test, HPLC, etc. When the glucose concentration drops, the glucose may be replenished by adding about 20% aliquots of the glucose-salts concentrate solution, while insuring that the total glucose concentration remains below about 30 g/L. In the initial phase, when high cell density is achieved and the glucose is substantially completely depleted, for about 2 to 4 hr thereafter, more usually about 3 hr thereafter, the glucose depleted state is maintained. Then, at relatively equal time increments thereafter, glucose may be added, so as to provide a rate of addition of about 0.005 to 0.015 g glucose/hr/g cells. At such time as the L-ascorbic acid concentration remains substantially constant or begins to decrease, the reaction is stopped, the cells and supernatant isolated and the ascorbic acid separated from the cells and collected in accordance with conventional ways.

In accordance with the subject method, high yields of L-ascorbic acid are obtained, far higher than those from other naturally occurring sources, such as rose hips. Levels exceeding 3.5% of biomass material can be achieved with levels of 4.0% and higher attainable. The concentration of L-ascorbic acid exceeds 1.45 g/L and can be 3.3 g/L or greater. Based on the substrate consumed, molar yields are at least about 0.010, usually at least about 0.013.

The following examples are offered by way of illustration and not by way of limitation.

EXPERIMENTAL

Sterilized in a 1L fermentor was 0.6 L water, 0.23 g dibasic sodium phosphate and 0.27 g monobasic potassium phosphate. To the phosphate solution was then aseptically added 11.2 mg of ferrous sulfate (heptahydrate) in 5 ml distilled water and 20 ml of sterile glucose-salts concentrate prepared as follows. Groups of nutrients sterilized individually and combined after cooling:

| | Group 1 |
|---|---|
| 56 g | glucose, food-grade monohydrate (anhydrous basis) (80 g/L) in 80 ml water |
| | Group 2 |
| 0.7 g | trisodium citrate dihydrate (1.0 g/L) magnesium sulfate anhydrous (0.66 g/L) and |
| 1 ml | sulfuric acid (1.4 ml/L) in 10 ml water |
| | Group 3 |
| 0.65 g | monobasic sodium phosphate (0.97 g/L) |
| 1.3 g | monobasic potassium phosphate (1.9 g/L) and |
| 0.68 g | dibasic sodium phosphate (0.97 g/L) in 10 ml water |
| | Group 4 |
| 9.4 ml | Trace Metal solution |

The temperature was raised to 35° C., agitation begun at about 200 rpm and 50 ml of *Chlorella pyrenoidosa* UV101-158 at a concentration of about 0.3 g cells/L added. These cells were deposited at the A.T.C.C. on June 27, 1985 and given Accession No. 53170. The following chart describes the conditions and analytical results for the fermentation.

TABLE 3

| Time hr | pH | Cell Density g/L | Ascorbic acid mg/L | Comments |
|---|---|---|---|---|
| 0 | 6.9 | — | | |
| 5 | 6.6 | 0.7 | | 400 rpm; air 0.4 l pm |
| 16 | 6.9 | 3.8 | | 550 rpm; air 0.6 l pm |
| 21 | 7.0 | 9.5 | | 700 rpm; add 20 ml* |
| 24 | 6.9 | 14.2 | | 800 rpm; add 20 ml* |
| 36 | | | | glucose depleted |
| 40 | 7.1 | 38.6 | 538 | add 4 ml+ |
| 45 | 7.2 | 38.6 | 654 | |
| 48 | | | | add 4 ml+ |
| 51 | 7.6 | 38.1 | 775 | add 2 ml+ |
| 65 | 7.7 | 37.8 | 966 | |
| 68 | 7.8 | | 1050 | add 4 ml+ |
| 92 | 7.6 | 37.2 | 1292 | |
| 101 | 7.3 | 36.1 | 1459 | |

*glucose/salts concentrate
+20% glucose. This addition was repeated periodically during the course of the fermentation.

The method employed for determining L-ascorbic acid is described by Grun and Loewus, *Analytical Biochemistry* (1983) 130:191-198. The method is an ion-exchange procedure, employing a 7.8×300 mm organic acid analysis column, HPX-87 (Bio-Rad Laboratories, Richmond, Calif.). The conditions are: mobile phase, 0.013 M nitric acid, flow 0.8 ml/min, pressure 1500 psig, detection, UV 245-254 nm. With the above conditions, resolution of L-ascorbic acid and isoascorbic is possible.

To determine the grams of cells per liter, the following procedure is employed. A biomass sample (5 ml) is transferred to one weighing pan and 5 ml of supernatant transferred to a second weighing pan. The supernatant is centrifuged. The pans are dried in a convection oven (105° C. for 3 hrs). After cooling in a desiccator, the pan contents are weighed. The grams of cells per liter are determined as: (sample weight − supernatant weight) × 200.

Based on the above results, specific formations based on grams of ascorbic acid per gram of cell are achieved of 0.04 or greater and the molar yield defined as moles of L-ascorbic acid formed per mole of glucose consumed is at least 0.01 or higher. In addition, the ascorbic acid concentration can be raised to about 1.5 g/L or higher.

It is evident from the above results that enhanced yields of ascorbic acid can be achieved with efficient utilization of glucose and fermentor time. Microorganisms, particularly Chlorella strains, can be grown in fermentors where high levels of L-ascorbic acid are obtained with efficient utilization of an inexpensive carbon source to provide L-ascorbic acid.

Although the foregoing invention has been described in some detail by way of illustration and example for purposes of clarity of understanding, it will be obvious that certain changes and modifications may be practiced within the scope of the appended claims.

What is claimed is:

1. A method for the production of L-ascorbic acid, which comprises:

growing *Chlorella pyrenoidosa* strain ATCC accession No. 53170 in a nutrient medium containing a glucose source in a range of about 15-30 g/L and low levels of iron and copper for a sufficient time to grow the cells to a density of about 35 to 45 g/L and subsequently complete depletion of the glucose source;

maintaining the glucose source depleted state for about 2 to 4 hours; and adding the glucose source at a rate of 0.005-0.015 g glucose/hr/gram cells to maintain a concentration less than 0.1 g/L until a level of L-ascorbic acid of at least about 1.45 g/L is obtained.

2. A method for the production of L-ascorbic acid, which comprises:

growing *Chlorella pyrenoidosa* ATCC accession No. 53170 in a nutrient medium containing a glucose source in about 15-30 g/L and having nonrepresenting levels for L-ascorbic acid production of iron and copper;

after substantially complete depletion of the glucose source, maintaining the glucose source depleted state for from 2 to 4 hours;

adding the glucose source at a rate of 0.005-0.015 g glucose/hr/gram cells to maintain a glucose source concentration less than 0.1 g/L until a level of L-ascorbic acid of at least about 1.45 g/L is obtained; and harvesting the cells and isolating L-ascorbic acid essentially free of other cellular materials.

* * * * *